US 6,490,530 B1

(12) United States Patent
Wyatt

(10) Patent No.: US 6,490,530 B1
(45) Date of Patent: Dec. 3, 2002

(54) AEROSOL HAZARD CHARACTERIZATION AND EARLY WARNING NETWORK

(75) Inventor: Philip J. Wyatt, Santa Barbara, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 0 days.

(21) Appl. No.: 09/577,108

(22) Filed: May 23, 2000

(51) Int. Cl.$^7$ ............................................... G01H 31/00

(52) U.S. Cl. .............................. 702/24; 702/23; 702/26

(58) Field of Search .............................. 702/24, 23, 26

(56) References Cited

U.S. PATENT DOCUMENTS

| | | | | |
|---|---|---|---|---|
| 3,612,689 A | * | 10/1971 | Liskowitz | 356/342 |
| 4,548,500 A | * | 10/1985 | Wyatt et al. | 356/336 |
| 4,710,025 A | * | 12/1987 | Wyatt et al. | 356/343 |
| 4,906,978 A | * | 3/1990 | Best et al. | 340/630 |
| 5,059,349 A | * | 10/1991 | Carlon et al. | 252/408.1 |
| 5,159,315 A | * | 10/1992 | Schultz et al. | 340/539 |
| 5,920,827 A | * | 7/1999 | Baer et al. | 702/3 |
| 5,956,145 A | * | 9/1999 | Green et al. | 356/364 |

* cited by examiner

*Primary Examiner*—John S. Hilten
*Assistant Examiner*—Stephen J. Cherry
(74) *Attorney, Agent, or Firm*—Philip J. Wyatt

(57) ABSTRACT

An aerosol hazard classification and early warning network is composed of a large number of detector and analysis units, called "detector stations," which are deployed throughout a region to be warned of a potentially hazardous aerosol intrusion. Such aerosol threats may originate from fires, volcanic eruptions, or overt releases of biological and chemical agents dispersed in aerosol form. Among the former are the characteristic toxic aerosols released during refinery fires or explosions. The latter biological agents include bacterial spores, lyophilized bacterial cells, and virus preparations, whereas chemical agents might include various forms of nerve gasses and other anti-personnel gasses such as mustard, all commonly deployed in aerosol form. Each detector station contains an aerosol handling unit that samples and transfers ambient aerosol particles one-at-a-time through a light scattering chamber where each such particle is constrained to pass through a fine laser beam producing, thereby, an outgoing scattered light wave. The scattering chamber contains a plurality of scattered light detectors arranged to accept light scattered into different angular locations. The signals detected at each detector position are processed by a corresponding digital signal processing chip with the resulting set of digitized signals being transferred to an on-board central processing unit. The CPU analyzes the set of light scattering signals and identifies or otherwise characterizes each particle. The classification/identification data are then stored and, on preprogrammed command, telemetered to a remote "central station" by means of an on-board telemetry unit. The central station analyzes the sets of data received from all the detector stations and then instructs, as necessary, selected detector stations via telemetric means to change their sampling and telemetry rates. As soon as sufficient data are available, the central determines the presence, threat, extent, and progress of the aerosol cloud. These factors are then telemetrically transmitted by means of alarms and warnings sent to potentially threatened regions.

46 Claims, 4 Drawing Sheets

AEROSOL HAZARD CHARACTERIZATION AND EARLY WARNING NETWORK

Figure 1:
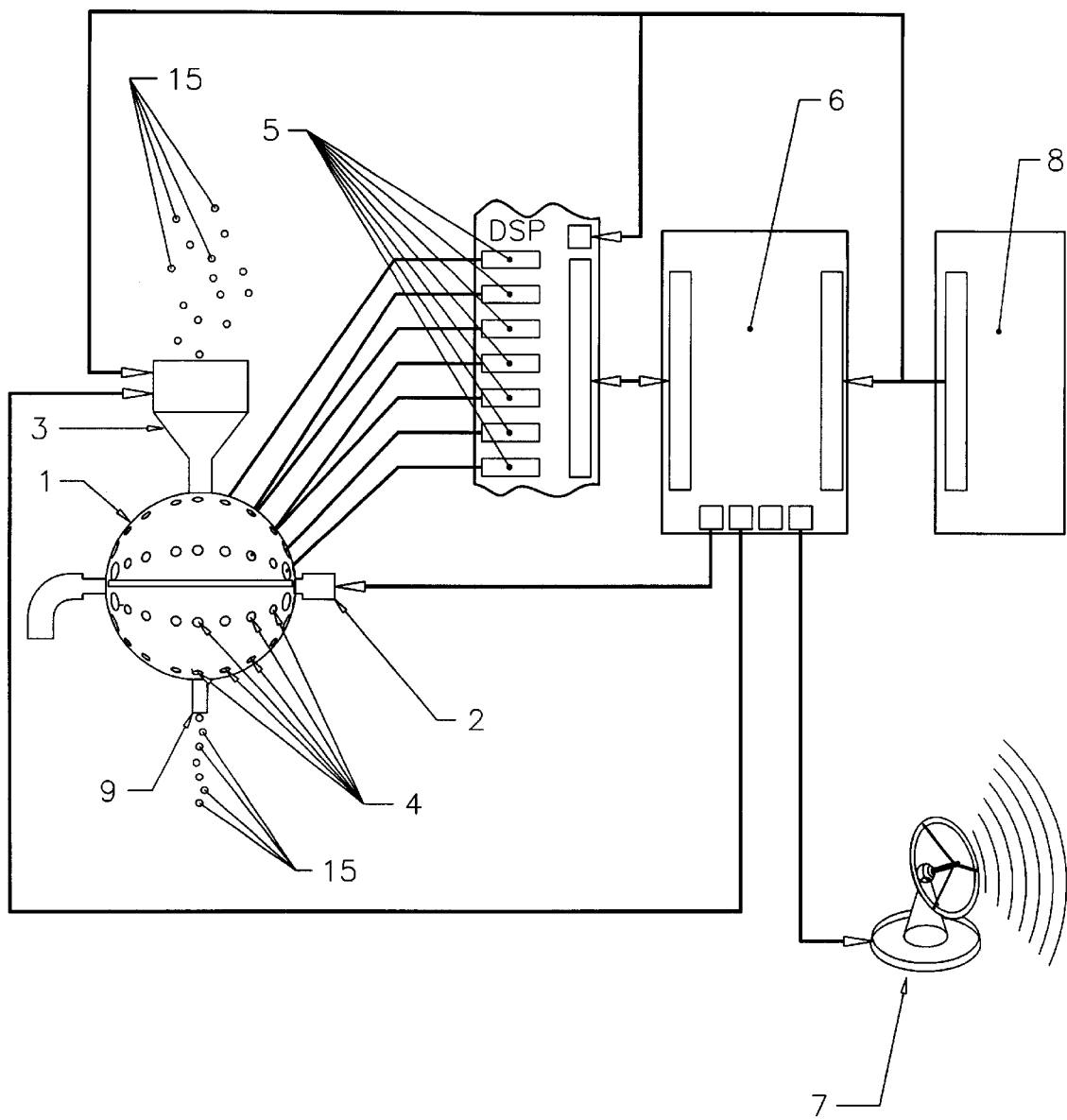

The present invention is concerned with a method and apparatus for monitoring the progress and composition of a cloud of aerosol particles that had been released previously into the atmosphere. By "progress" is meant position and concentration relative to a region for which said aerosol cloud may pose a health hazard.

Expressly incorporated herein are the following patents concerning means and techniques by which such aerosol constituents of the cloud may be classified and/or identified:

4,548,500—"Process and Apparatus for Identifying or Characterizing Small Particles." (Oct. 22, 1985).

4,693,602—"Method and Apparatus for Measuring the Light Scattering Properties of Small Particles." (Sep. 15, 1987).

4,710,025—"Process for Characterizing Suspensions of Small Particles." (Dec. 1, 1987).

BACKGROUND

Most of the aerosol particles present in the Earth's atmosphere pose little or no health hazard. Even the occasional dangerous aerosol particle is of negligible importance because its concentration is so low However, when pathologically hazardous aerosol particles occur in great numbers, their potential to cause illness or injury increases dramatically The presence of high concentrations of such aerosol particles can occur naturally or from man made sources. Volcanic eruptions are examples of the former while accidental chemical plant releases and refinery plant explosions are representative of the later.

Other natural releases of potentially dangerous aerosols include those occurring during the rapid formations of photochemical smogs, often initiated by manmade contributions such as automobile exhaust products. The natural releases of fungal spores, such as Coccidiodes immitis, the causative agents of coccidioses, under the occasional environmental conditions needed to promote the rapid growth and maturation of the parent fungi, can have devastating effects on the health of those affected. Finally, there is a large range of potentially lethal aerosols that might be released by terrorist or military groups intent on inflicting great numbers of casualties. These include aerosols of both biological and chemical origin and their release is generally expected to be surreptitious.

When dangerous aerosol particulate clouds occur within or adjacent to populated areas, it is desirable to provide an early warning for the inhabitants that might be affected were they to inhale such aerosols. Such warnings can result in a dramatic reduction of casualties in spite of the possible unpredictable collateral responses, such as civil unrest due to fear or panic, by the endangered population. It has often been reasoned that by the time such aerosol threats are detected and identified, it is too late to issue a warning to the potentially affected population. This is not generally true.

Aerosol intrusions often occur as dispersals in the form of clouds released above the ground. For example, volcanic eruptions generally send huge quantities of material into the upper atmosphere from which the aerosol particles fall back to the earth and only affect the local populations once they reach near ground levels. In ambient air, a particle of radius $10^{-6}$ m=1 $\mu$m and density of 1 gm/cm$^3$ would require almost 3 hours to fall just one meter. Thus with a suitably deployed warning system, the threat posed by such aerosols will be ascertained long before they reach altitudes or locations where their presence might cause injury.

There are many types of aerosols that are harmless. Obvious examples are water droplets or even fine ice mists. It is important that any viable warning system be able to differentiate between potentially dangerous aerosols and the more common harmless varieties.

The means by which aerosol threats to a local population be recognized is an important object of this invention. Obviously, for volcanic eruptions or chemical plant explosions or similar aerosol intrusions, the source and location of the resultant aerosol cloud is easily noted and tracking is often straightforward, except perhaps at night if visual means are used. This type of daylight tracking is generally passive and based on the observation of the effect of such intrusive clouds upon background illumination. Knowing the source of the cloud means that its composition is also known, at least initially. Instrumentation may be brought into the affected regions for purposes of local compositional monitoring that, eventually, forms the basis for evacuation planning if needed. Additionally, once a potentially threatening aerosol cloud has been detected, its monitoring may be achieved to some degree by optical or radio wave probing of the cloud using laser or radio sources at a safe distance from the threat.

A popular concept for providing warning of an aerosol threat is based on a traditional RADAR approach using laser produced radiation to probe the cloud threat at a distance. NASA had applied such techniques in their extensive measurement programs of 1989 through 1990 as a means for the profiling of aerosol and cloud backscatter, Doppler wind measurements, and the measurement of atmospheric trace species. Despite exceedingly large Federal expenditures in this area, the technique is not expected to yield any practical optical signals capable of permitting cloud composition to be deduced. Nevertheless, for clouds of known origin, composition may be deduced based on such a priori information. Ulich et al. in their U.S. Pat. No. 5,257,085 discuss many elements and variations of this technique for probing the physical properties of distant scenes by use of both active and passive interrogations.

The LIDAR (light detection and ranging) technique has various faults including requirements for an unimpeded view of the aerosol, i. e. without intervening particulates, atmospheric interferences, or opaque structures. Inferring aerosol concentrations from such LIDAR measurements of unknown particles is unlikely. Mixed aerosol compositions as well as size distributions that are changing in time illustrate further shortcomings of the concept. Esproles, in his U.S. Pat. No. 5,345,168, has explored some novel means for improving the information content in the returned LIDAR signal. Min et al. in their U.S. Pat. No. 5,102,218 discuss LIDAR measurements at very short ranges, generally less than 30 meters, for extracting target signatures from mixtures of target components and naturally occurring aerosol particles. The referenced patent's detailed description includes many references to the target aerosol discrimination techniques used for so-called active optical proximity sensors together with extensive discussion of the then-current state-of-the-art.

Stewart et al. in their U.S. Pat. No. 4,687,337 discuss the need to deduce the extinction coefficients of aerosol particles by means of instrumentation taken to the various sites to be studied. Such so-called point source or in situ measurements are contrasted in their patent to the conventional LIDAR measurements. However, bringing instrumentation and personnel into regions thought to contain dangerous aerosol particles is usually avoided. For this reason, remote-sensing techniques for probing suspected targets have always been considered preferable. Carrieri in his U.S. Pat. No. 5,241,179 discusses this requirement in greater detail explaining the research programs of the U. S. Army Research, Development, and Engineering Center from the 1960s. The objective of these programs was the development of remote sensors ". . . for detecting threat chemical and biological agents in vapor cloud, aerosol, rain, and . . . " as surface contaminants. A need for passive spectroscopic techniques was recognized in the early 1970s. Such techniques would collect and process radiance from natural or preexisting sources.

Advanced development on a remote chemical agent detection unit began in 1979. As of the filing of the Carrieri patent in late 1992, the differential scattering/differential absorption LIDAR devices, referred to simply as DISC/DIAL devices, were said to show the most promise and were considered the most technologically advanced vapor detection and range resolution systems currently in operation. Carrieri's invention purported to extend these capabilities by means of a related standoff detection technology that could sense contaminants on/within terrestrial and manufactured surfaces using their infrared absorption/emission signatures permitting, thereby, personnel ". . . to protect themselves and take appropriate action to decontaminate, or avoid contaminated areas altogether." These concepts still represented a far cry from the initial objectives for the remote characterization of aerosol particles and associated biological agents. There can be no doubt, reading these reports and the associated instrumentation descriptions, that ultimately some form of in situ detection and analysis would be needed.

Muran et al. hoped to address the need for in situ monitoring by means of their invention filed in 1998 and issued as U.S. Pat. No. 5,898,373. The method disclosed provides for the seeding of the regions to be interrogated at some future time with ". . . sticky polymeric particles" that would adhere to the various local surfaces for long periods of time. Using spectrophotometer equipped airborne vehicles, the reaction of these specially prepared particles with dangerous chemicals or particles would produce characteristic emissions capable of detection by the airborne instrumentation. Alternatively, the region seeded with the sticky particles could be scanned from above using active laser systems to induce excitation emissions from the materials/particles "trapped" by or adhering to the sticky particles. The sticky particles would be designed to incorporate suitable chemicals that would react with the target agents resulting in a unique photometric signature of the selected target candidates. The ability of these particles to be observed at the moment of their deployment could be considered fortuitous, at best, since each threat must have to have been anticipated by the appropriate deployment/seeding of a unique detector particle Much Federal finding has been directed during the past 50 years to problems associated with the protection of military personnel from aerosol threats, usually in the form of biological and chemical weapons. Small portable field instruments that would be able to identify small samples with great speed have received considerable support. Additionally, the hope to develop ". . . revolutionary point-detection technologies . . . that [include] detection devices [that] can be small (hand-held) instruments for individual soldier use . . . " has long been sought by the Government for protection of military personnel. The quotation referenced above is from a late 1999 request for proposals by the Defense Advanced Research Projects Agency (DARPA) in which they delineate their so-called "wish list." Although the concept of networking such devices is suggested, portability in the field is stressed.

Unfortunately, the DARPA emphasis, discussed above, falls short of a practical approach in several regards: First, is the lack of a warning system for purposes of alerting the civilian population of an impending threat. The first detection with such DARPA devices would occur when the individual carrying the device enters the field or is enveloped in the threat cloud. There is no attempt to develop an early warning system. Next, this particular procurement devotes extraordinary attention to the need of avoiding false positive alarms despite the fact that the mere presence of a biological aerosol itself is cause for immediate concern and alarm. Naturally occurring biological aerosols are extremely rare events.

Key to any warning system is the ability to detect the aerosol threat as soon as possible after it has been released. Once an aerosol threat has been released, the local concentrations of the offending particles are extremely high. For example, it has been estimated recently, following the analyses of the Russian anthrax accident at their Sverdlovsk facility, that about 10 viable spores of B. anthracis are required in the lungs of a healthy individual to cause disease. This would require ambient concentrations of the order of tens of thousands per liter of air. To achieve such concentrations, the aerosol concentrations near the release zone would require the presence of at least $10^6$ to $10^7$ per liter of air. Accordingly, near the release point, classification/identification becomes a much-simplified task because of the expected similarity of each member of the aerosol cloud ensemble. Finding a suitable signal becomes far simpler if detection is prompt and close to the release: an objective of the present invention. In such a huge collection of positively identified aerosol particles, the probability of misclassifying the entire ensemble, and thus the detected event itself, becomes vanishingly small. It is a major objective of the present invention to focus "on the forest," so to speak, rather than a particular "tree."

Additional emphasis of the DARPA procurement, which is typical of those issued by the Federal Government during the prior 30 years, is placed upon the need to differentiate between live and dead biological particles in the threat aerosol cloud. The belief that confirmation of the fact that because a threatening aerosol contains an overwhelming quantity of dead microorganisms, there are no remaining dangers associated with the trace viable cells cannot be considered a valid analysis of such a threat. The detection of the presence of potential pathogens, irrespective of their viability, is an essential element of any early warning system.

Threats associated with chemical agents are addressed also by various Federal procurement activities. One of the more interesting is the Shipboard Automatic Liquid Agent Detector (SALAD) program whose specification and related solicitations have long been in progress. ". . . The SALAD acquisition program has been initiated to provide the Navy with the capability to automatically detect liquid chemical warfare agents. This acquisition program has been underway for approximately five years during which the Government has developed and produced a prototype SALAD that has been analyzed and tested to confirm its potential to meet Navy operational requirements . . . " Later, within the specifications, it is stated ". . . The SALAD shall automatically detect liquid nerve (G- and V-series) and blister (H- and L-series) agents at the concentrations and droplet sizes as follows:—concentration: 2.0 mg/m2 and higher-droplet size: median mass diameter of 500 micrometers and larger {Objective–200 micrometers and larger} . . . " What is particularly striking about this activity is the enormous size associated with the median size: 500 μm. At this size in ambient air, the particle will fall 1 meter in about 22 seconds. The detection system has 60 seconds to make an identification of the agent and issue a warning within which time the particle would have fallen almost 3 meters. Detection issues are complicated farther by the ship's motion as well as ambient wind effects on moving the agents. Associated with such large particles are expected to be smaller particles that may well be undergoing evaporation. It is this latter fraction of a deployed chemical agent aerosol that would be most usefully detected since the aerosol's associated size distribution would be changing in time. It is a further objective of the present invention to monitor the size distribution and its changes with time as a means for detection of such agents. Natural aerosols comprised of water particles would exhibit similar behavior except for a very important and easily detected difference: the refractive index of water droplets is expected to be about 1.33 in contrast to that of a typical chemical agent. The present invention will extract the refractive index of selected aerosol particles as required from their recorded light scattering characteristics.

It is an object of the present invention to provide an explicit means to detect and monitor the composition of a potentially threatening aerosol cloud arriving at remote locations by remotely positioned detector means. Such detectors, called "detector stations," are capable of performing a set of scattered light measurements by which the target aerosol particles are well classified and/or identified, one-at-a-time, at each locale where they are detected. Each detector station transmits its collected and processed information by telemetric means to a central station that is responsible for further processing of the received data. Important among the latter processing activities is the prediction of the movement of all elements of the aerosol cloud.

Another objective of this invention is to process further the reduced data received by transmission means from each deployed detector station to permit prediction of arrival time and threat danger to sites not yet exposed to said aerosol cloud. A means by which air mass movement could be followed is described in U.S. Statutory Invention Registration # H111 issued Aug. 5, 1986 to Barditch et al. Their tracking technique seems of little practical consequence since they must seed the air mass to be monitored at one location with *Bacillus thurengiensis* spores and then culture a sample of air collected at a second location. The subsequent growth on a specially prepared culture plate of the seed spores confirms the origin of the sampled air and the numbers recovered a measure of the diffusion of the seeded sample during its journey. This method is inapplicable as a warning system and requires the a priori detection and location of the aerosol threat. Sometimes, should the aerosol threat be detected or noticed and if it is known to contain spores or other culturable organisms, such sampling may provide a historical record of the threat, but no warning. Interestingly, and as a consequence of the present inventive method, the bacterial spore seeding implementation of Barditch et al. could easily be replaced thereby using polystyrene latex spheres of nominal diameter 1 μm. Since such particles are readily detected in real time with an element of the present invention, results can be almost instantaneous since no time- and labor-consuming culturing would be required.

Another objective of the invention is to provide rational central station decisions, based upon analyses of all data collected from the set of deployed detector stations, to provide an alarm and/or warning of the expected arrival time of the dangerous aerosol cloud and its probable composition and suggested means for protection of the soon-to-be-exposed populations. This alarm and warning is prepared for each locale on an individually calculated basis. Thus one region might be given a ten-minute warning whereas another simultaneously might receive a two-hour warning. Each such report to each specified locale is updated in a timely manner and communicated to each potentially affected locale to insure maximal warning for the threatened population.

A further objective of the invention is to use the central station to regulate data collection and analysis rates at each detector station, collectively or individually, by telemetry means.

There are many different means for characterizing aerosol particles at a fixed location. For example, Cole in his U.S. Pat. No. 5,296,910 describes the use of multiple force fields combined with Doppler velocimetry to obtain particle density, diameter, electric charge, magnetic moment, and other physical attributes of individual particles. Gerber in his U.S. Pat. No. 5,315,115 describes optical means of determining particulate integrated properties that could then be used to classify an aerosol in terms of its integrated volume concentration, integrated surface area concentration and aerosol extinction coefficient in the infrared spectral region. The text "Modern methods of particle size analysis" edited by Howard Barth (Wiley-Interscience, New York 1984) discloses a large number of techniques by which the aerosol particle sizes may be determined. Theodore Provder has edited several collections of papers for the American Chemical Society Symposium Series on the analysis and characterization of particles and particle size distributions under the title "Particle size distributions I, II, and III" in 1987, 1992, and 1998. There are literally hundreds of texts and thousands of scientific articles on related topics of particle characterization. There is, however, one technique with the greatest breath of application for aerosol particle characterization.

The most powerful technique for differentiating and characterizing individual aerosol particles is by means of light scattering. In their broadest sense, light scattering measurements are performed using a collimated monochromatic light beam through which the particles pass, generally one-at-a-time. During its transit through the beam, a particle scatters some of the light incident upon it. This scattered light is then collected by means of collimated detectors positioned at discrete scattering angles with respect to the direction of the incident light beam. Each detector may be fitted with various optical elements including polarizing analyzers, interference filters, electrooptical shutters, neutral density filters, waveplates, and other optical elements. Even in its simplest implementation, with all detectors lying in a plane and no analyzer at any detector, Wyatt and his co-workers have demonstrated the powerful characterization capabilities of the technique including the following:

For determining the refractive index and size of simple, homogeneous polystyrene latex particles "Measurement of the Lorenz-Mie Scattering of a Single Particle: Polystyrene Latex," with D. T. Phillips and R. M. Berkman, J. of Colloid and Interface Science 34, 159 (1970):

For the study of bacterial spores

"Dielectric Structure of Spores from Differential Light Scattering," *Spores V,* American Society for Nicrobiology, (1971);

"Observations on the Structure of Spores," J. Applied Bacteriology 37, 48 (1975);

For the detection and characterization of photochemical smog particles
"Single Particle Light Scattering Measurement: Photo-Chemical Aerosols and Atmospheric Particulates," with D. T. Phillips, Applied Optics 11, 2082 (1972);
For differentiating aerosolized bacterial cells
"Structure of Single Bacteria from Light Scattering," with D. T. Phillips, J. Theor. Biol. 37, 493 (1972);
For measuring the accretion of acid-like coatings on aerosol particles generated by power plants
"Some Chemical, Physical and Optical Properties of Fly Ash Particles," Applied Optics 14, 975 (1980);
The detector system described in U.S. Pat. No. 4,693,602 by Wyatt et al., as well as in the paper:
"Aerosol Particle Analyzer," with Y. J. Chang, C. Jackson, R. G. Parker, D. T. Phillips, S. D. Phillips, J. R. Bottiger and K. L. Schehrer, Applied Optics 27, 217 (1988), represents an early version of a more general detector incorporating out-of-plane measurements as well as depolarization analyzers. This earlier device as disclosed and implemented was very large, requiring an argon-ion or HeCd laser as an illumination source and individual photomultiplier detectors connected to a read head by means of optical fibers. Accordingly, it had a very high power consumption that made it difficult to operate on battery supplies for extended periods of time. The photomultiplier power supplies and assorted computer and aerosol handling systems added further bulk and cost to the analyzer making it impractical for any type of field deployment.

In order to monitor successfully potentially dangerous aerosol threats and differentiate them from harmless constituents, a large number of individual light scattering detector stations must be placed strategically around and throughout the region to be protected. Although the concept of a "point source" detector, i. e. one that is localized and restricted in its range of detection, has been recognized for many years, the concept of linking such detectors cooperatively in a network and providing individual detectors the means to function filly and independently in classifying the local aerosols it may sample has not been considered previously and represents a further objective of this invention.

Networked detectors have been used extensively for telecommunications purposes and similar techniques of lid localized detector units have been used frequently to provide fire and intruder protection for buildings and similar regions. Such so-called wireless warning systems employ a variety of signal processing techniques to insure high reliability. For example, Sanderford et al. in their U.S. Pat. No. 5,987,058 employ a spread spectrum technology with high reliability for the continuous monitoring of a building. Sheffer et al. in their U.S. Pat. No. 5,568,53 5 describe explicitly a cellular alarm unit that includes cellular phone functions permitting cellular connections to remote monitoring stations. The remote monitoring stations detect an emergency condition by means of sensors that preferably include fire sensors, perimeter sensors for detecting opening of doors or windows, for example, and a panic switch for activation by an individual within the enclosed area in the event of a medical or other emergency. The Sheffer et al. system is intended to circumvent more conventional hard-wired systems that are easily defeated by severing the traditional telephone wiring. There are many other types of alarm systems that provide for efficient, cost-effective and reliable cellular-type radio/telephone communication system included within an alarm system to provide wireless communication such as described by Smith et al. in their U.S. Pat. No. 4,993,059.

All of the aforementioned alarm systems that make use of a network of cellular or other wireless intercommunications means are based on sensors intended to detect and then warn of a class of easily monitored phenomena. Most important among these are fire and smoke detection, intruder presence, physical parameters such a temperature and humidity, panic alarms, television monitoring stations, radiation detection, etc. As will be evident from the detailed description of the present invention, the sensors used therein are both distinct and uniquely different from sensors of these types in the following ways: the sensors provide for data collection and real-time processing and analysis; the sensors incorporate a variety of electrooptical elements as well as a fully functional microprocessor; they can be reprogrammed, the sensors include means for sample handling.

Each station must be capable of processing the data it collects and telemetering the results to a central station that would collect such results from all stations for subsequent analysis and make decisions concerning alarms or other warnings. Despite the existence of a wide range of analytical tools for the counting, sizing and classifying aerosol particles, there has been no attempt to integrate some of these tools with a means for appraising the threat of an aerosol intrusion and alerting the targeted population of the need to protect itself. The present invention discloses a straightforward means by which this may be achieved.

BRIEF DESCRIPTION OF THE INVENTION

The invention disclosed here describes a means, comprised of an array of light scattering detector stations and their ancillary electronic and physical infrastructure, by which communities, buildings, compounds, military bases, airports, embassies, parks and other selected regions may be warned of the presence of an impending aerosol threat. Key to the successful operation of such a system are detector stations capable of preparing ambient air samples for measurement, measuring and classifying aerosol particles therein one-at-a-time using multiangle light scattering over a broad range of discrete scattering angles, identifying specific threat subclasses from the data so-collected and analyzed within the collected aerosol sample, counting relative numbers of such subclasses, monitoring physical changes that may be occurring throughout the analysis period, and reporting all processed data via integrated telecomnunications links to a central control station.

Each light scattering detector station includes a scattering chamber traversed by a fine laser beam, together with the capability to: dilute the sampled aerosol stream so that only a single particle is in the beam at any moment; make light scattering measurements on each transiting particle over a broad range of discrete scattering angles using detectors that may incorporate polarization and fluorescence analyzers; and, process the data collected identifying, thereby, the type and class of each aerosol particle measured. Data processing and classification are achieved using an integrated microprocessor system that contains random access memory and read only memory incorporating the preprogrammed software required for particle classification. In addition, each such station has a compact transmitter similar in concept to the GHz transmitters used by conventional cellular telephones.

Each detector station, which has been sited previously to form a component of a multi-detector network spanning the region to be monitored, is connected via a telecommunications link to a central station The central station receives and processes all data transmitted from the linked detector stations. On the basis of such processed data, the central station monitors the aerosol cloud's position and composition, evaluates all potential threats to the region being monitored, commands specific detector stations as required to change or modify such detectors' specific collection rates and processing, and issues alarms and/or near real-time warnings to subregions of any potential problems expected from the aerosol cloud.

BRIEF DESCRIPTION OF THE DRAWINGS

FIG. 1 shows the major components of a typical Detector Station.

FIG. 2 is an internal view of a typical scattering chamber for making MALS measurements from aerosol particles, one at a time.

FIG. 3 is an example of a Detector Station deployment

FIG. 4 shows details of the Central Station

DETAILED DESCRIPTION OF THE INVENTION

The present invention makes use of the sampling and analytical capabilities of a large number of sophisticated detector stations to appraise and track the movement of and dangers posed by an aerosol cloud or dispersal. Each detector station collects and processes the light scattering signatures of individual sampled particles of the incident aerosol ensemble and then classifies or identifies each such particle. Incorporated in each station is a complete sampling capability that entrains sampled aerosol particles within a particle free air sheath and transports them one-at-a-time through an incident beam of monochromatic light. The detector station contains also means to detect the subsequently scattered light over a broad range of discrete scattering angles. These scattered light signals are processed digitally by electronic means and transmitted to a central processing unit, CPU, means for subsequent classification and processing. Once a predetermined quantity of aerosol particles have been so-processed, their identification, size distribution and other derived features are telemetered to a central station. The central station, which receives the analytical results of the many detector stations, must then correlate the data, determine the cloud's composition, estimate its movement, predict its potential effects on the threatened population, and initiate appropriate alarms and warning signals to protect said population.

In their preferred embodiment, the detector stations of the present invention are compact, use small yet powerful solid-state lasers, have built-in hybrid photodiode detectors each of which has an associated digital signal processing (DSP) chip, and incorporate a complete microprocessor system including random access memory and programmable memory. The DSP chip may be replaced with any combination of electronic components that will achieve the same objective, i e. find the peak scattered light signal at each detector as the scattering particle passes through the laser beam and convert such signals into a digital form for subsequent processing. This could be accomplished for each detector by means of separate peak detector circuits, sample-and-hold circuits, and an analog-to-digital converter.

A key element of each detector station is its aerosol handling capability, discussed above, by which aerosol particles incident upon the detector station may be sampled and drawn into the scattering chamber by laminar flow means, said laminar flow also providing sufficient dilution to insure that the aerosol particles pass through the incident laser beam one-at-a-time. The aerosol handling functions are all under the control of the same on-board computer that receives the digitally processed light scattering signals from the each of the station's detectors. The rate at which these signals are received provides the basis for the on-board computer to regulate dilution and laminar flow speeds An event counter, also under the control of the computer, provides data that are combined with the dilution status to generate instantaneous particle number density. The processed light scattering data permit subsequent calculation of the differential size fraction distributions for each class of particles detected, or just the predominant type according to programming.

The preferred embodiment of the individual detector stations operates in a manner to conserve power whenever possible. For example, the light source, preferably a solid state laser such as a GaAs laser operating with an output power level of about 30 mW at a wavelength of around 680 nm need be activated at a very low duty cycle. It may be turned on to sample ambient air periodically, say, once every two minutes and then for a duration of only a few seconds. This reduced duty cycle can be changed rapidly whenever directed to do so by the central station or automatically whenever there is a significant change of events in the sampled aerosol. The background aerosol load is expected to be quite low. Filter means may be provided also to remove large aerosol aggregates confirmed to pose no dangers for the monitored region.

The telemetry means incorporated into each detector station permits data processed by the detector station's on-board computer to be transmitted in real time to the central station that monitors the evolution of the reports received from the individual stations, makes judgments as to the extent of the aerosol threat, if any, and determines the type of warning required for each region specified as protected. The central station can transmit commands to each or any of the detector stations to change local data acquisition rates and modify duty cycler, as needed. The central station also can modify data processing protocols, i e. the analytical software on-board each detector station.

The integrated computer/microprocessor of each detector station is generally preprogrammed to analyze the digitized multiangle light scattering signals collected from each traversing aerosol particle. From these analyses, the microprocessor must catalog each aerosol particle among the classes preprogramyned and store such information together with an on-going enumeration for each designated class. Periodically, these processed data are transmitted by telemetric means to the central control station. The central station can, of course, modify the processing software at each detector station. This would be the case were the individual particle events found to produce scattering patterns subsequently classified as due to similar particles, simplifying, thereby, subsequent analysis to classify newly detected particles. Such a modification would speed up the on-board processing of the detector station significantly. The central station or each detector station individually, in response to a perceived or anticipated threat, may determine the most suitable rate of transmission based on pre-established parameters. Thus an individual detector station subject to a rapidly changing aerosol load may increase its sampling and transmnission rates. The central station, on the other hand, aware of anomalously high data processing events at certain detector stations, may send specific instructions to a selected set of such detector stations to change their processing and/or transmission rates.

The identification, classification, or characterization of each aerosol particle whose light scattering properties have been collected during its traversal through the illuminating light beam of each detector station is based on subsequent on-board analyses of such data. In the preferred embodiment of this invention, some of the individual detectors located about the scattering chamber will include special optical analyzers in front of them. Thus if the incident light is plane polarized with respect to a particular scattering plane, as will be the case for the preferred embodiment, some detectors may include polarzation analyzers so that depolarization effects may be monitored. It may be desirable also to place an electrically adjustable waveplate before some detectors such as a liquid crystal retarder. In this marner, it is possible to obtain the Stokes parameters of each scattering particle usefull for further classification. Other elements that may be combined with the individual detectors include narrow bandpass filters that permit measurement of particle fluorescence when the output of such elements is compared to equivalent elements absent such filters.

In the preferred embodiment of the invention, the detectors are high gain transimpedance photodiodes of the type manufactured, for example, by United Detector Technologies. These would be mounted directly into the scattering chamber that incorporates the necessary collimators associated with each detector. Naturally, there are many other types of detectors that may be employed similarly including photomultipliers, avalanche photo diodes, and even CCD arrays. If the detector element must be isolated from the scattering chamber for environmental reasons, then they may be interfaced by optical fiber means.

FIG. 1 presents a schematic layout of an individual detector station. It is anticipated that of the order of 50 such units would be required to monitor a small building complex, whereas as many as 10,000 to 500,000 might be required for a small city. For the latter cases, it may be desirable to provide several central stations coordinated through a master station. The scattering chamber 1 contains the light beam source 2, preferably a solid state laser diode incorporating suitable collimating and beam focusing elements so as to produce a plane polarized beam passing generally along a diameter of said scattering chamber. In the preferred embodiment of the scattering chamber, its structure is that of a spherical shell. The ambient aerosol samples are introduced into the scattering chamber and diluted under control of the detector station's central processing unit 6 by means of the aerosol-handling module 3. The photo detectors 4 are mounted preferably in the scattering chamber's outer surface and, in the preferred embodiment of the invention, are high gain transimpedance photo diodes. Each detector subtends a fixed solid angle at the aerosol particle/laser beam region of intersection and thus receives a corresponding fraction of the light scattered by the aerosol particle throughout the particle's period of passage through the laser beam. In the preferred embodiment of this system, the detectors will be positioned at discrete angular locations lying on great circles whose common center is the point of intersection of the particle stream with the laser beam. If the laser produces plane polarized light, as will be the case generally, then detectors lying on the great circle for which the laser beam lies along a diameter are among the most important for the subsequent measurements to be made. For this plane so-defined, the polarization of the laser beam is chosen preferably to be perpendicular to this scattering plane. Some of the. detectors mounted on the scattering chamber will be fitted with optical analyzers shown in further in FIG. 2

The aerosol particles 15 are conveyed through the scattering chamber by means of a particle-free laminar flow sheath provided by the aerosol-handling module 3. In such a manner, each entrained particle will intersect the beam at the center of the scattering chamber before exiting the scattering chamber at exhaust port 9. A DSP 5 programmed to fit analytically the time-versus-intensity profile collected in the DSP's RAN memory, processes the signal produced by each detector. Since the laser beam profile generally will have a gaussian profile, each detector will generate a series of digitally encoded intensity values that will follow such a gaussian profile as scattered light data is collected and converted during the particle's passage through the beam. The DSP chip will process these data points and obtain the maximum value recorded which is then transmitted to the CPU module 6. The complete set of intensity values produced by the corresponding set of detectors is then analyzed by the CPU to yield the identification or classification of the scattering particle. Some sets of intensity values will be ignored and not classified furthers following instructions from the CPU-based program.

The CPU will collect and process such identification or classification results to determine other aerosol particle properties following the on-board CPU instructions. Among such properties would be the types of particle classes cataloged as well as the calculated size distribution of each class. Periodically, and again under on-board program commands collected and processed data are telemetered to the central station via the telemetry module 7. Such hole may receive also program modifications from the central station that are transferred to the CPU module 6 for immediate implementation. For example, such a modification may be implemented by the CPU to increase th e detector station sampling rate by causing the aerosol handling system to decrease its dilution of the sampled aerosol. All elements of the detector station receive power from the power supply modules which may be connected directly to an external power grid, be sustained by on-board battery sources, or by such on-board batteries continually recharged by external grid power such as found in conventional emergency lighting devices or by a solar power panel.

Figure 2:
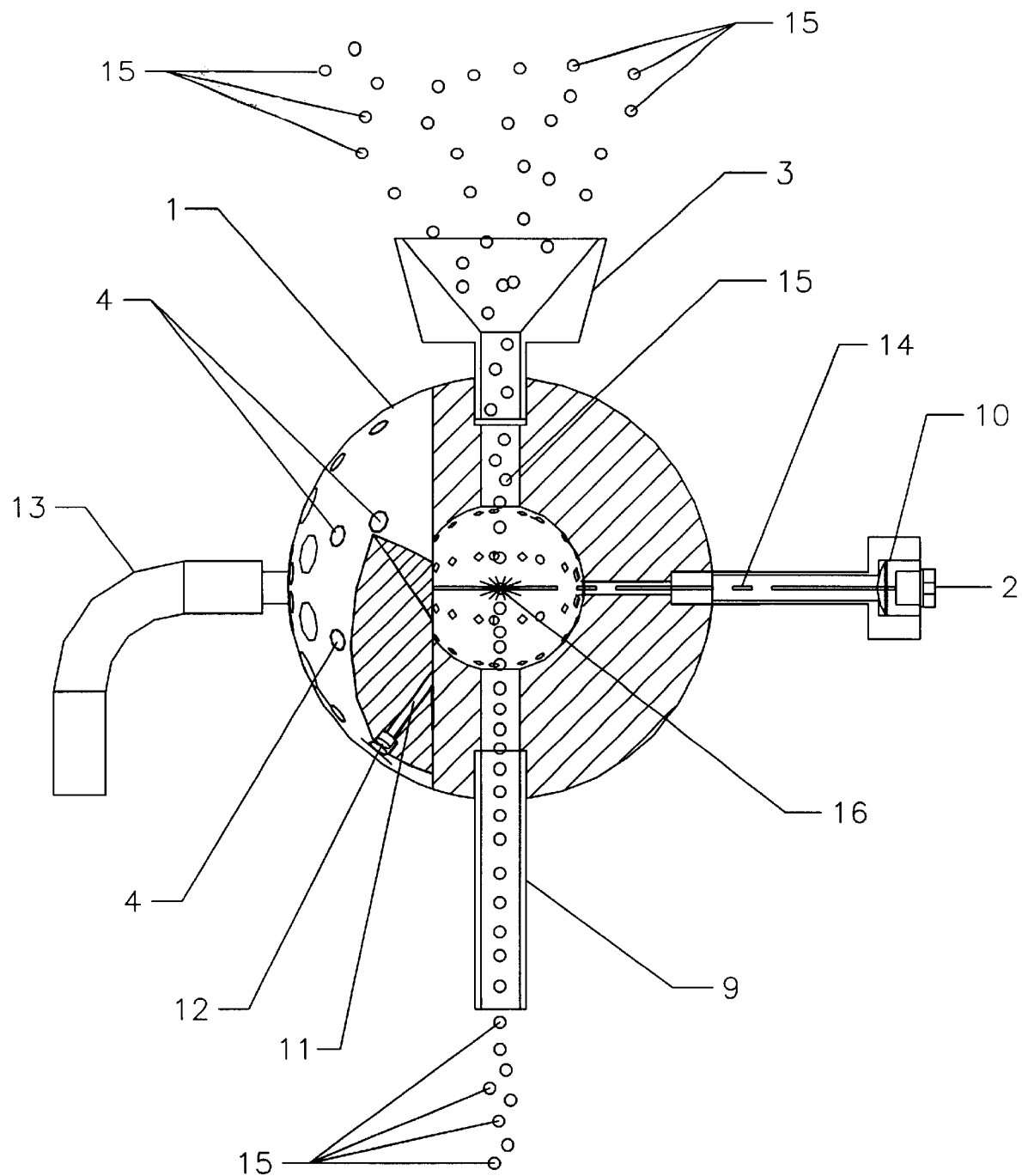

FIG. 2 presents an interior view of a spherical scattering chamber 1. The atmospheric aerosol is sampled by means of the aerosol handling system 3. This system includes components to filter air used to dilute the sampled aerosol and transport the aerosol particles 15 one-at-a-time in a sheath flow through the scattering chamber, exiting at the outflow orifice 9. Diluted samples are thus delivered in the sheath flow through the laser beam 14 that lies along a diameter of the chamber. The laser beam is produced by the fight source 2 after collimation by its associated collimator 10 and exits the scattering chamber 1 at the light trap 13 As discussed above, a particle 15 passing through the laser beam 14 produces an out going spherical scattered wave, emanating from the beam/particle intersection region 16, intercepted by detectors 4 mounted in the scattering chamber. Each detector is collimated by means of channels 11 preferably cut into the chamber wall. Said channels may contain additional optical elements to restrict further a detector's field of view and solid acceptance angle with respect to the scattering event occurring at 16. Such elements 12 may be masks, simple lenses, or analyzers such as polarizers, optical waveplates to produce various retardations, interference filters for the measurement of fluorescence and other inelastic scattering phenomena.

In order to obtain sufficient light scattering data, a sufficient number of detectors must be utilized. As discussed earlier, the detectors are generally placed on great circles for scattering chambers of near spherical shape. The range of polar angles chosen will lie generally between 5° and 175° and the azimuthal angles over the find 360° range. Previous studies of particles whose root mean squared radii lie below 1000 nm have shown that of the order of 10 to 30 such detectors, suitably fitted with optical elements such as polarizing analyzers and interference filters, are sufficient to yield discriminating optical observables by which means broad classes of aerosols may be differentiated. On the other hand, if the particles being detected are found to be of the same class and only subsequently detected members of this class only are to be enumerated, then the number of detectors and the range of scattering angles required may be reduced significantly. Although a detector station configured in the preferred embodiment may have 30 detectors, collection of all of their associated signals may not be necessary once the predominant classes of aerosol particles have been identified. By reducing the number of detectors required for particle classification, the sampling rate may be increased accordingly. The selection of which detector signals are used may be done on-board each detector station on the basis of a decision mad by its CPU or following direction from the central station.

Figure 3:
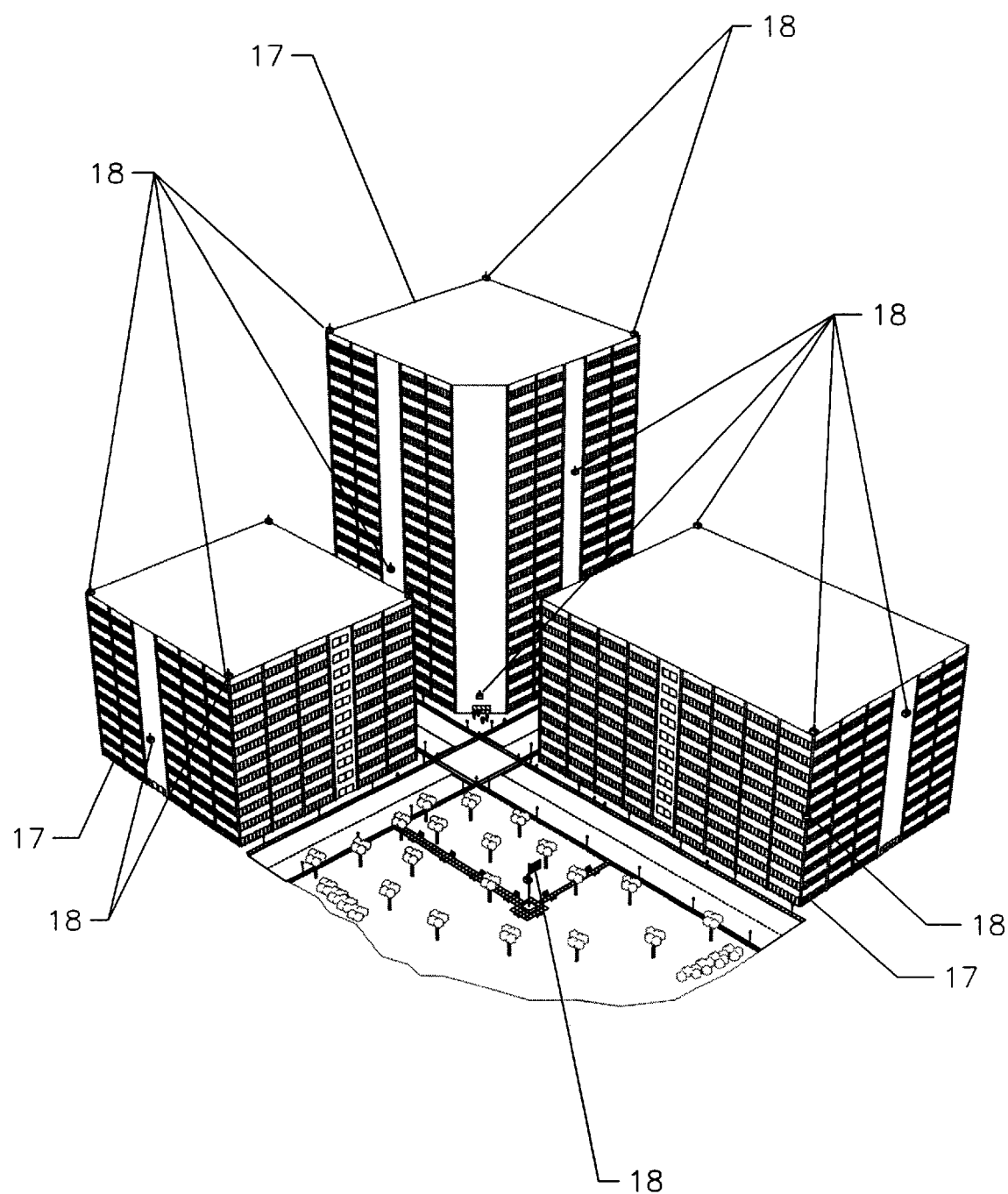

FIG. 3 shows a small complex of buildings with a small park area 17 whose protection against an aerosol intrusion is desired. Accordingly, detector stations 18 are deployed throughout the complex. Many will be placed on buildings at various locations, on walls and throughout the key interior regions of the buildings themselves. The latter would include air registers and any open window locations. Preferably, most of the detector stations affixed to outer building surfaces will be at heights of several meters above the ground such as roof areas by which means airborne releases of aerosols will be detected early relative to the appearance of the aerosol at the more threatening ground levels.

Figure 4:
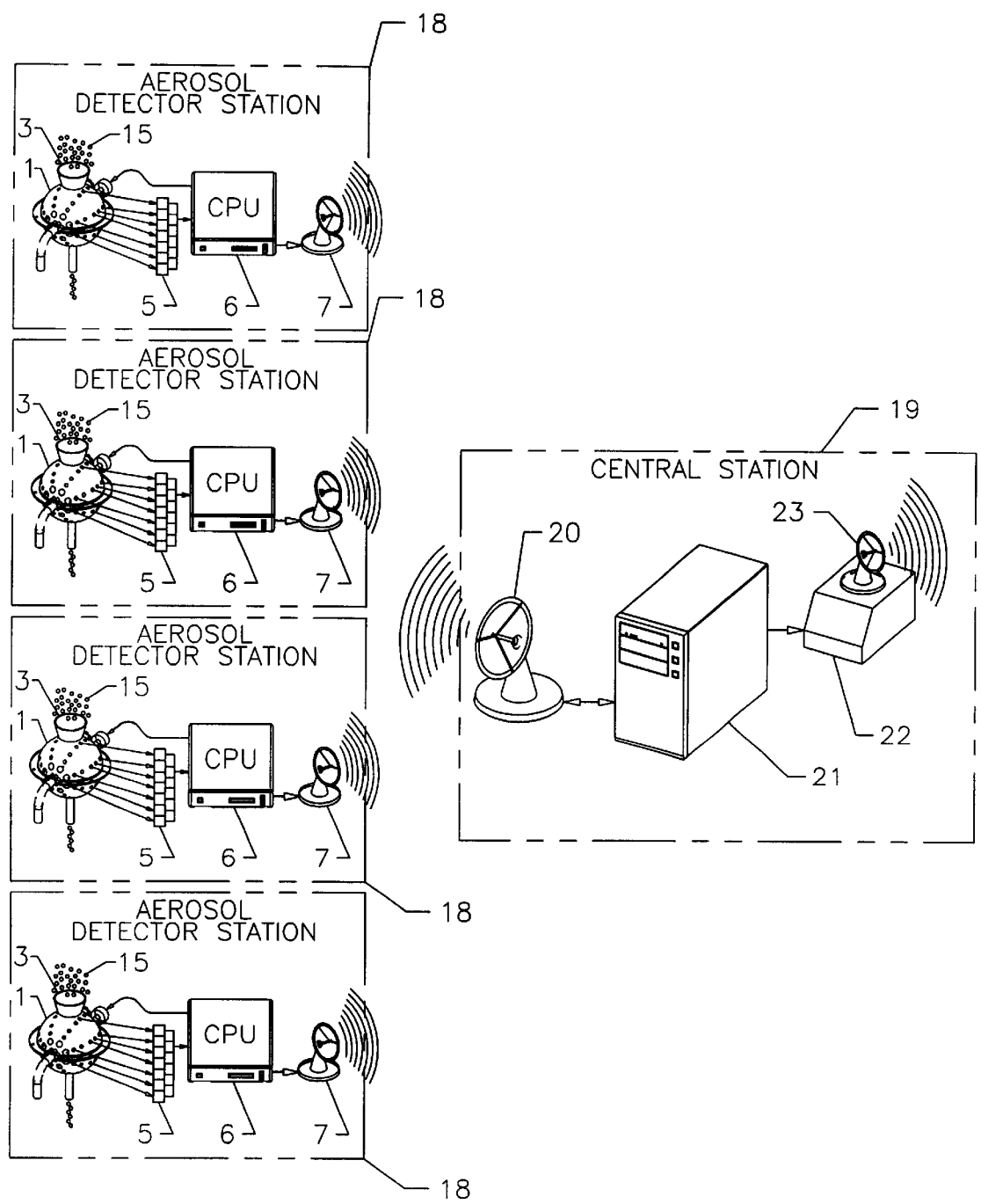

FIG. 4 presents an overview of the aerosol hazard characterization and early warning network, the subject of this invention. Several detector stations 18 are shown schematically with their scattering chambers 1, sampled aerosol particles 15, aerosol-handling units 3, DSP chips 5, CPU 6, and transmitter 7. The central station collects, buffers, and processes the data sets received from the plurality of detector stations 18, via its communications/telemetry module 20, in its CPU unit 21. This unit includes telemetry switching and collection modules, central RAM and ROM memory together with large storage capability. As the number of detector stations controlled by a central station becomes larger, the central station CPU capabilities must increase, as well. It may be necessary to divide detector stations into sub-groups, each controlled by a central station, with the central stations themselves controlled by a master station Pre-loaded software analyzes threat potential and anticipated aerosol cloud movement. The latter function is significantly simplified in the present invention because the detector stations are widely dispersed. As an aerosol cloud moves, the rate at which threat particles are detected by individual stations yields an immediate measure of cloud movement and diffusion. Increasing event rates indicates that the cloud is moving into the region being monitored whereas decreasing rates suggest that the threat elements are leaving the region. Such data would be integrated with more general meteorological data if and when available. Such monitoring is extremely important to follow the elevation of the threat cloud as particles begin to fall out of higher release altitudes into the characteristically lower populated regions. From such threat analyses, the central station warning and alarm processor 22 sends updated information by alarm telemetry means 23 to various civil, police, emergency, and other agencies responsible for population health and safety throughout and surrounding the monitored region. Such information includes estimates of threat characteristics, suggested activity to minimize casualties, aerosol movement and prognosis, evacuation suggestions, protection strategies, etc. The central station CPU unit 21 communicates also via communications/telemetry module 20 with computer selected detector stations instructing them to modify the following, as appropriate, sampling rates, analytical software, data transmission rates, calibration, etc.

Many types of aerosols become affixed to the soil once they fall to that level. This is particularly true of biologically based aerosols including those that might be used for terrorist purposes. The key for an early warning system is to detect the particles before they reach levels at which the local populations would be most affected. The July-August 1999 issue of the journal Emerging Infectious Diseases, published by the National Center for Infectious Diseases, center of the Centers for Disease Control and Prevention, reprints key papers presented at the National Symposium on Medical and Public Health Response to Bioterrorism held in Arlington, Va. on Feb. 16 –17, 1999. Among the papers presented are two that describe distinct attacks on population centers by deployment of a bio-aerosol. A paper by Inglesby describes in considerable detail an attack using anthrax spores released by a truck driving along an elevated road near a stadium where 74,000 people are attending an evening football game. ". . . As it passes the stadium, the truck releases an aerosol of powdered anthrax over 30 seconds, creating an invisible odorless anthrax cloud more than a third of a mile in breadth. The wind [a gentle breeze blowing from west to east] blows the cloud across the stadium parking lots, into and around the stadium, and onward for miles over the neighboring businesses and residential districts. After the anthrax release the truck continues driving and is more than 100 miles away from the [stadium] . . . by the time the game is finished . . . The driver of the truck and his associates leave the country by plane that night . . . " The author estimates that approximately 16,000 of the 74,000 attendees will have been infected while another 4000 would be infected in the business and residential districts downwind of the release which, of course, is detected by no one. The author subsequently describes the epidemiology of anthrax cases caused by the release and the difficulties that traditional laboratories have in diagnosing the illness properly.

With the present invention, the scenario during and following the anthrax spore release will be changed significantly. During the release, the detector stations mounted atop and throughout the stadium will detect and classify the release and its probable composition. This information will be transmitted to the central station almost immediately which, in turn, will result in a public announcement at the stadium. This announcement will be presented calmly, explaining the possibility that a dangerous release has been detected and then instruct the attendees-to take immediate action in the form of covering their heads and faces with cloth or garments, to lie down and breath slowly through the preferably wettened cloth, and await further instructions for an orderly evacuation. In addition, the surrounding detector stations will now be increasing their sampling and reporting rates under control of the central station. With the new flow of reports coming into the central station, the central station itself will be sending warnings to the threatened populated areas with frequent updates of aerosol movement and instructions for protecting the local population. The local medical treatment facilities will have been alerted also so they will be better prepared to diagnose properly the new patients that will be visiting in the days ahead. In addition, the release and its detection at the stadium will have triggered the central station to reprogram surrounding detector stations to begin more frequent sampling in the immediate vicinity of the primary release. In this manner, it becomes possible to track the releasing vehicle and estimate its potential route and alert law enforcement authorities to intercept the vehicle. By virtue of this implementation of the preferred embodiment of this invention, the casualties will be reduced significantly, perhaps to fewer than 1000.

The paper by O'Toole on pages 540–546 describes a scenario concerning an attack of unknown origin involving the purported use of aerosolized smallpox virus in an unknown carrier. No means or location is given for the release of the aerosol. Only the subsequent epidemiology and confusions, again, with accurate diagnoses of the infected population are discussed It appears highly certain that were the preferred embodiment of the present invention suitably deployed, the location and time of the initial release would have been determined together with the progress of the aerosol well before any illness were detected. Such warning and cloud tracking insure further that the clinical stations, such as emergency rooms who would receive critically ill patients, would have been forewarned as to the probable cause of such illnesses.

There are many environmental issues that have not been discussed earlier concerning detector station deployment. Because many such stations will be placed in outdoor locations, they will be subject to large variations of weather including extreme summer heat, cold winters, rain, snow, icing conditions, high winds, etc, Accordingly, they must be protected from the effects that such variations might have on the ability of the units to function properly. In this regard, some units will require special hardening against the various environmental elements. It may be necessary to provide adequate insulation and perhaps even environmental control. For example, a well-insulated unit might include a Peltier heater/cooler to maintain a stable local operational environment.

Other detection and early warning concepts have been discussed in the background section of this disclosure. One of the important objectives of the LIDAR systems, for example, is to look for characteristic signatures of potential biological threats. Fluorescence and UV activity are often accompanying signatures of a biological agent. Although the present invention can make fluorescence measurements on individual particles at longer wavelengths than that of the incident radiation by means of interference filters as earlier disclosed, it would be a simple matter to add a pulsed UV source to the scattering chamber whereby the fluorescence response from a single particle so-stimulated could be detected, The decision to look for such signatures in addition to the multiangle scattering pattern could be under the detector station's CPU control or, as received from the central station. Such pulsing could be coincident with the incident scattering radiation or separately applied instead of it. There are many variations of such ancillary measurements easily understood by those skilled in the art of UV stimulation of biological materials.

The powerful detector stations disclosed in this invention are capable, as has been described, of a variety of analytical processes. In addition to particle characterization and identification, such stations can collect sets of data, compare with previous data sets, determine size distributions as well as changes in such distributions, and numerous other functions well within the capabilities of a CPU interfaced with a data generation and collection system Table 1 below is an example of the type of data that might be telemetered by a detector station of the present invention that processes the vast array of data that it collects. This simulated collection set would have been transmitted on Jun. 8, 2002 at 2:28 PM from detector station 314. The time interval since the last transmission, $\Delta\tau$, from this station was 2 minutes and 15 seconds. For these particular samplings, transmissions at intervals less than 1 minute were not needed. Two major classes of aerosol particles were detected and classified G and K, respectively. Minor constituents were not classified, The root mean square radius for class 1 (corresponding to G particles) was 940 nm and that of class 2 (K particles), 320 nm. The change in rms radius since the last transmission for class 1 was ±10 mn while that of class 2 had decreased by 50 nm. The full width at half maximum, FWHM, for class 1 was 10 nm while that for class 2 was 75 nm. The change of the FWHM for class 1 in the 2 minutes and 15 seconds since the last transmission from this station was zero whereas that for class 2 had increased by 20 nm. The calculated particle concentration, $n_1$, for class 1 taking into account sample dilution, was 250 per ml while that of class 2, $n_2$, was 700 per ml. The corresponding changes in concentration for the two classes during the 2 minute 15 second interval were both decreases of 200 and 350 particles per ml, respectively. Finally, the dilution factor used by the aerosol handling module during the reported transmission was 1:30. The change of dilution factor since the last transmission was a decrease of a factor of 20. Thus the previously transmitted data were based on a dilution factor of 1:50 compared to the present 1:30. The ambient density is thus decreasing thereby decreasing the amount of dilution required. Transmission of the simulated data set of Table 1 requires a negligible bandwidth. The set of measured and derived variables that might be transmitted conveniently from even a large set of detector stations involving several thousand stations could be expanded to include other variables such as fluorescence response and various particle morphological parameters thus could be expanded significantly without seriously impeding data collection and analysis by the central station.

The simulated data of Table 1 show characteristics of the two types of particles classified. For this particular simulation, it was assumed that only the two dominant particle classes be enumerated. Both classes G and K show a decrease in concentration over the 2 minutes and 15 seconds between collections. Class G appears to have a stable size with an unchanging rms radius and full width of the size distribution at half maximum, FWHM. Class K, on the other hand, shows a marked increase in its FWHM and a significant decrease in its rms radius. Accordingly, these and similar deductions can add further information to help classify and identify the classes detected.

TABLE 1

| Typical telemetered data (simulated) | |
|---|---|
| Time & detector stamp | 06080214:28#314 |
| $\Delta\tau$ | 000215 |
| Particle Class 1 (nm) | 940 |
| Particle Class 2 (nm) | 320 |
| rms 1 (nm) | 940 |
| rms 2 (nm) | 320 |
| $\Delta r$ 1 | ±010 |
| $\Delta r$ 2 | −050 |

TABLE 1-continued

Typical telemetered data (simulated)

| Time & detector stamp | 06080214:28#314 |
|---|---|
| FWHM 1 | 010 |
| FWHM 2 | 075 |
| ΔFWHM 1 | 0 |
| ΔFWHM 2 | −020 |
| $n_1$ | 250 |
| $n_2$ | 700 |
| $\Delta n_1$ | −200 |
| $\Delta n_2$ | −350 |
| Dilution factor | 30 |
| Δ[Dilution factor] | −20 |

Although the preferred embodiments of the aerosol hazard early warning system have been listed explicitly, there are many variations that will be obvious to those skilled in the art of aerosol characterization and which are hereby incorporated by reference into this disclosure.

I claim:

1. An aerosol hazard characterization and early warning network comprising
   A) a plurality of detector stations positioned throughout the physical region to be protected thereby where each detector station is comprised of
      i) a light scattering chamber module containing
         (a) an aerosol sampling and handling module;
         (b) a plurality of scattered light detectors;
         (c) a light source producing a monochromatic collimated beam of light traversing a central plane of said chamber;
      ii) electronic circuitry converting analog signals produced by said detectors into digital representations thereof;
      iii) a central processing unit containing memory and processing means together with controlling and processing software that
         (a) controls said aerosol sampling and handling system;
         (b) stores digital data produced from each particle light scattering event occurring as said aerosol particle crosses said collimated beam of light;
         (c) analyzes said data to characterize each aerosol particle from said particle's set of stored digitized light scattering signals;
         (d) processes and stores the ensemble of said analyses of said characterized particles for subsequent transmission;
      iv) a telemetry communication system that
         (a) sends processed data analyses to a central station;
         (b) receives modifying control, processing, and transmission instructions from a central station;
   B) a central station that receives processed data from each of the detector stations, sends, if deemed necessary, each detector station modified sampling instructions based on said central station analysis of data received therefrom, analyzes data received from said detector stations to establish aerosol source cloud extent and movement, and communicates by telemetric means early warnings of threats posed by said cloud through said region to be protected, said central station is comprised of
      i) a telemetric transmitting and receiving module;
      ii) a central processing unit, CPU, containing switching and buffering means permitting data transmitted from all detector stations to be received and stored;
      iii) analytical software permitting said CPU to analyze and process data so-received and to modify, as required, the sampling and analytical processes performed by each said detector station;
      iv) separate telemetric module to transmit appropriate warnings to said protected region of immanent threats based on said analyses and suitable measures suggested to mitigate said threat.

2. The aerosol hazard characterization and early warning network of claim 1 where said monochromatic collimated beam of light is plane polarized.

3. The aerosol hazard characterization and early warning network of claim 1 where said plurality of detectors include some that have been fitted with analyzers placed before them.

4. The aerosol hazard characterization and early warning network of claim 1 where said plurality of detectors lie along great circles with respect to the center of said light scattering chamber.

5. The aerosol hazard characterization and early warning network of claim 1 where said electronic circuitry converting each analog signal produced by each of said detectors into a digital representation thereof consists of a preprogrammed digital signal processing chip.

6. The aerosol hazard characterization and early warning network of claim 1 where said detector stations are powered by an on-board battery source.

7. The aerosol hazard characterization and early warning network of claim 1 where said detector stations are powered by line source with a battery backup source.

8. The battery-powered network of claim 6 where said battery is maintained charged by solar cell charging means.

9. The aerosol hazard characterization and early warning network of claim 4 where said plurality of detectors include some that lie in a plane perpendicular to the plane of polarization of said monochromatic beam of light.

10. The aerosol hazard characterization and early warning network of claim 3 where said analyzers are narrow band pass filters preventing thereby all light from entering said detector to which it is affixed of wavelength different from the wavelength incident upon the scattering particles.

11. The aerosol hazard characterization and early warning network of claim 3 where said analyzers are plane polarizing and are affixed to detectors lying in a plane perpendicular to the plane of polarization of said incident beam.

12. The aerosol hazard characterization and early warning network of claim 1 where said CPU of each said detector station calculates the mean size, size distribution, and changes in said mean size and size distribution of said characterized particles.

13. The aerosol hazard characterization and early warning network of claim 1 where said light source is a laser.

14. The aerosol hazard characterization and early warning network of claim 13 where said laser is a GaAs solid state laser.

15. The aerosol hazard characterization and early warning network of claim 13 where power output of said laser is of the order of 30 mW.

16. The aerosol hazard characterization and early warning network of claim 1 where said aerosol sampling and handling module dilutes said sampled aerosol source cloud and transports individual aerosol particles within a sheath flow through said scattering chamber, said monochromatic light beam, and exiting through an exhaust port.

17. The aerosol hazard characterization and early warning network of claim 1 where said plurality of detectors are high gain transimpedance photodiodes.

18. The aerosol hazard characterization and early warning network of claim 3 where said analyzers include optical waveplates.

19. The aerosol hazard characterization and early warning network of claim 3 where said analyzers include electrically adjustable liquid crystal retarders.

20. The aerosol hazard characterization and early warning network of claim 19 where said processing software permits said detector station CPU to calculate Stokes parameters for each aerosol particle for which digitized detector signals have been collected.

21. The aerosol hazard characterization and early warning network of claim 1 where said light scattering chamber module includes UV light excitation source.

22. The aerosol hazard characterization and early warning network of claim 1 where said detector station scattered light detectors whose digitized signals are to be processed and analyzed by said detector station CPU are placed at polar angles between 5° and 175° and azimuthal angles between 0° and 360°.

23. A method for providing early warning of an impending aerosol threat to a designated physical region comprising the steps of
   a. placing throughout said physical region a plurality of detector stations where each detector station contains
      i. a light scattering chamber module means comprised of
         1. an aerosol sampling and handling means;
         2. a plurality of scattered light detector means;
         3. a light source producing a monochromatic collimated beam of light traversing a central plane of said chamber;
      ii. electronic circuitry means converting analog signals produced by said detectors into digital representations thereof;
      iii. central processing unit means containing memory and processing means together with controlling and processing software that
         1. controls said aerosol sampling and handling system;
         2. stores digital data produced from each particle light scattering event occurring as said aerosol particle crosses said light beam;
         3. analyzes said data to characterize each aerosol particle from said particle's set of stored digitized light scattering signals;
         4. processes and stores the ensemble of said analyses of said characterized particles for subsequent transmission;
      iv. a telemetry communication means to
         1. send processed data analyses to a central station;
         2. receive modifying control, processing, and transmission instructions from a central station;
   b. receiving processed data from each of said detector station means at a central station means that would send, if deemed necessary, to each detector station means modified sampling instructions based on said central station means analysis of data received therefrom, to analyze data received from said detector station means to establish aerosol source cloud extent and movement, and to communicate by telemetric means early warnings of threats posed by said cloud through said region to be protected, said central station consists of
      i. a telemetric transmitting and receiving means;
      ii. a central processing unit means, CPU, containing switching and buffering means permitting data transmitted from all detector stations to be received and stored;
      iii. analytical software means permitting said CPU to analyze and process data so-received and to modify, as required, the sampling and analytical processes performed by each said detector station;
      iv. separate telemetric means to transmit appropriate warnings to said protected region of immanent threats based on said analyses and suitable measures suggested to mitigate said threat.

24. The method for providing early warning of an impending aerosol threat to a designated physical region of claim 23 where said monochromatic beam of light is plane polarized.

25. The method for providing early warning of an impending aerosol threat to a designated physical region of claim 23 where said plurality of scattered light detector means include some that have been fitted with analyzers placed before them.

26. The method for providing early warning of an impending aerosol threat to a designated physical region of claim 23 where said plurality of scattered light detector means lie along great circles with respect to the center of said light scattering chamber.

27. The method for providing early warning of an impending aerosol threat to a designated physical region of claim 23 where said electronic circuitry means converting each analog signal produced by each of said scattered light detector means into a digital representation thereof consists of a preprogrammed digital signal processing means.

28. The method for providing early warning of an impending aerosol threat to a designated physical region of claim 23 where said detector station means are powered by an on-board battery means.

29. The method for providing early warning of an impending aerosol threat to a designated physical region of claim 23 where said detector station means are powered by line source with a battery backup source.

30. The method of claim 29 where said battery means is maintained charged by solar cell charging means.

31. The method for providing early warning of an impending aerosol threat to a designated physical region of claim 26 where said plurality of scattered light detector means include some that lie in a plane perpendicular to the plane of polarization of said monochromatic light beam.

32. The method for providing early warning of an impending aerosol threat to a designated physical region of claim 25 where said analyzer means are narrow band pass filter means preventing thereby all light from entering said scattered light detector means to which it is affixed of wavelength different from the wavelength incident upon the scattering particles.

33. The method for providing early warning of an impending aerosol threat to a designated physical region of claim 25 where said analyzer means are plane polarizing and are affixed to scattered light detector means lying in a plane perpendicular to the plane of polarization of said incident light beam.

34. The method for providing early warning of an impending aerosol threat to a designated physical region of claim 23 where said CPU means of each said scattered light detector station means calculates the mean size, size distribution, and changes in said mean size and size distribution of said characterized particles.

35. The method for providing early warning of an impending aerosol threat to a designated physical region of claim 23 where said light source means is a laser.

36. The method for providing early warning of an impending aerosol threat to a designated physical region of claim 35 where said wavelength of light produced by said laser is of the order of 680 nm.

37. The method for providing early warning of an impending aerosol threat to a designated physical region of claim 36 where said power output of said laser is of the order of 30 mW.

38. The method for providing early warning of an impending aerosol threat to a designated physical region of claim 23 where said aerosol sampling and handling means provides means to dilute said sampled aerosol source cloud and means to transport individual aerosol particles within a sheath flow means through said scattering chamber means, said light beam, and exiting through an exhaust port means.

39. The method for providing early warning of an impending aerosol threat to a designated physical region of claim 23 where said plurality of scattered light detector means are high gain transimpedance photodiode means.

40. The method for providing early warning of an impending aerosol threat to a designated physical region of claim 25 where said analyzer means include optical waveplate means.

41. The method for providing early warning of an impending aerosol threat to a designated physical region of claim 25 where said analyzer means include electrically adjustable liquid crystal retarder means.

42. The method for providing early warning of an impending aerosol threat to a designated physical region of claim 41 where said processing software means permits said detector station CPU means to calculate Stokes parameters for each aerosol particle for which digitized detector signals have been collected.

43. The method for providing early warning of an impending aerosol threat to a designated physical region of claim 23 where said light scattering chamber means includes UV light excitation means.

44. The method for providing early warning of an impending aerosol threat to a designated physical region of claim 23 where said detector station scattered light detector means whose digitized signals are to be processed and analyzed by said detector station CPU means are placed at polar angles between 5° and 175° and azimuthal angles between 0° and 360°.

45. The aerosol hazard characterization and early warning network of claim 13 where said laser source is a GaAs solid state laser.

46. The method for providing early warning of an impending aerosol threat to a designated physical region of claim 23 where said light source is a laser.

* * * * *